United States Patent [19]
Ducret et al.

[11] Patent Number: 5,635,614
[45] Date of Patent: Jun. 3, 1997

[54] SUGAR/SUGAR ALCOHOL ESTERS

[75] Inventors: Amélie Ducret, Montreal; Robert Lortie, Outremont; Michael Trani, Lasalle, all of Canada

[73] Assignee: National Research Council of Canada, Ottawa, Canada

[21] Appl. No.: 489,138

[22] Filed: Jun. 9, 1995

[51] Int. Cl.$^6$ .................. C07G 3/00; C12P 19/44
[52] U.S. Cl. ............ 536/18.6; 536/115; 536/119; 127/2; 127/30; 127/46.1; 127/53; 435/74; 435/921
[58] Field of Search ............... 536/18.6, 115, 536/119; 127/2, 30, 46.1, 53; 435/74, 255, 921

[56] References Cited

U.S. PATENT DOCUMENTS

| | | | |
|---|---|---|---|
| 5,200,328 | 4/1993 | Kirk et al. | 435/101 |
| 5,273,898 | 12/1993 | Ishii | 435/198 |

OTHER PUBLICATIONS

Fregapane et al, "Enzymatic Solvent–Free Synthesis of Sugar Acetal Fatty Acid Esters" Enzyme Microb. Technol, 1991, vol. 13, Oct. pp. 796–800.

*Primary Examiner*—Nathan M. Nutter
*Attorney, Agent, or Firm*—J. Wayne Anderson

[57] ABSTRACT

The invention disclosed relates to a process for the preparation of sugar and sugar alcohol esters of general formula I $$(R\!-\!COO\!-\!)_n\!-\!R^1 \qquad (I)$$

wherein R is an alkyl group, $R^1$ is derived from a sugar or a polyol moiety and n is 1 to 3, comprising reacting a sugar or a polyol with an acyl moiety, such as a carboxylic acid or ester, in a suitable solvent therefor and in the presence of an enzymatic catalyst capable of catalyzing the formation of ester bonds, and under reduced pressure sufficient to vaporize the solvent and by-product water, and continuously removing the water.

17 Claims, 1 Drawing Sheet

* 15 ml of an aqueous solution of biosurfactant + 10 ml of xylene.
** 20 ml of an aqueous solution of biosurfactant + 5 ml of xylene.

SUGAR/SUGAR ALCOHOL ESTERS

FIELD OF THE INVENTION

This invention relates to a process for the preparation of sugar and sugar alcohol esters.

Fatty acid esters of sugars and sugar alcohols constitute a very interesting group of non-ionic surfactants with potentially important applications in many industries because of their surface active properties due to their composition. This type of amphiphilic molecule has very good emulsifying, stabilizing or conditioning effects. In addition to be the conjugates of renewable feedstocks, inexpensive and readily available, they are not harmful to the environment because they are completely biodegradable under aerobic and anaerobic conditions, they are non-toxic, non-skin irritants, odourless and tasteless and they give normal food products after human and animal digestion. For all those reasons, they can be used in numerous areas particulary for enhanced oil recovery, in environmental detoxification processes, in pharmaceutical, detergent, cosmetic, food, and agricultural industries.

In spite of the above mentioned advantages, synthesis of esters of sugars or sugar alcohols is limited. Such products are obtained with difficulty by standard chemical esterification, because these techniques involve high temperatures which cause coloration of the final products and dehydration and cyclization in the case of sugar alcohols. To overcome these problems, esters of sugars or sugar alcohols can be prepared with a biological catalyst under very mild conditions, but they have not been used on a large scale in industry because of the disadvantages associated with the preparation thereof.

DESCRIPTION OF THE PRIOR ART

The synthesis of sugar esters has been reported by Seino et al. in aqueous media between different sugars (sucrose, glucose, fructose, sorbitol) and fatty acids (stearic, oleic, linoleic acids) in J. Amer. Oil Chem. Soc. vol. 61, 1984, page 1761–1765. Also see U.S. Pat. No. 4,614,718. However, this technique using the lipase of Candida cylindracea does not give significant quantities and cannot be used for industrial purposes.

Various authors (Therisod et al., J. Am. Chem. Soc., vol 108, 1986, page 5638–5640; Riva et al., J. Am. Chem. Soc., vol 110, 1988, page 584–589; Chopineau et al, Biotechnol. Bioeng., vol. 31, 1988, page 208–214) have made sugar esters with porcine pancreatic lipase, Chromobacterium viscosum lipase or subtilisin (Bacillus subtilis protease) in organic solvents in which both sugars and fatty acids are soluble. The yield is better but they use solvents such as pyridine or dimethylformamide, both very toxic substances and absolutely non-compatible with industrial purposes. Furthermore, to increase the rate of the reaction, they use trichloroethylesters of fatty acids instead of fatty acids, which are also non-compatible with industrial purposes.

Khaled et al. have done the synthesis of sugar esters with Lipozyme (Mucor miehei lipase) in tertiary alcohols (French Patent no. 2 646 439; Biotechnol. Lett., vol. 13, 1991, page 167–172). These polar alcohols can solubilize fatty acids, some sugars and sugars alcohols without any reactivity. Still, for many sugars, solubility is very low (glucose and saccharose for example).

In order to increase the solubility, it has been proposed to use organicboronic acids which are known to solubilize sugars in non-polar organic solvents by forming a carbohydrate-boronate complex by reversible condensation with carbohydrates. In this case, yields obtained in closed vials are noticeably increased (Schlottenbeck et al., Biotechnol. Lett., vol. 15, 1993, page 61–64; Oguntimein et al., Biotechnol. Lett., vol. 15, 1993, page 175–180; Ikeda et al., Biotechnol. Bioeng., vol.42, 1993, page 788–791). However, the fact that esterification is an equilibrium reversible reaction must be kept in mind. Indeed, the presence of the reaction products in the media limits the reaction to a maximum that cannot be theoretically exceeded in stoppered reactors. Besides, water liberated by the reaction affects directly the activity of the lipase which is known to have its maximum esterase activity within a strict hydration range.

To displace the equilibrium of the reaction, some researchers have performed the synthesis under reduced pressure in a solvent-free process. Therefore, the water liberated by the reaction is vaporized and eliminated without inhibiting the esterase activity of the enzyme and thus, favouring synthesis. However, the starting molten materials are not miscible together, and no reaction appears until substrate miscibility is increased. To overcome this problem, sugar acetals or sugar alkyl glucosides must be used. In addition, obtained products are not even the desired products since they do not show the desired properties. Further chemical transformations must be performed to yield the desired compounds (Fregapane et al., Enzyme Microb. Technol., vol. 13, 1991, page 796–800; Bjorkling et al., J. Chem. Soc., Chem. Comm., vol. 14, 1989, page 934–935; Bjorkling et al., Synthesis, vol. 2, 1990, page 112–115; Kirk et al., Biocatalysis, vol. 6, 1992, page 127–134).

The situation can be summarized as follows:

In the literature, three major problems inherent in the reaction are displayed:
1: The starting materials (sugar or sugar alcohol and fatty acid) have opposite polarities.
2: Esterification between a fatty acid and an alcohol is a reversible reaction leading to limited ester yields.
3: Water generated by the reaction increases significantly the water activity of the media, which in turn affects the esterase activity of the enzyme (biocatalyst inhibition), if it is not removed.

SUMMARY OF THE INVENTION

The method according to the invention takes care of all three problems presented above inherent in sugar ester synthesis by carrying out the reaction at once in solvent media and under reduced pressure. The originality of the process involves drying the solvent in a continuous fashion as follows: the pressure is lowered so that the solvent containing water is allowed to reflux thus vaporizing at the reaction temperature. Next, it is recondensed and is dried by passing through a water trap (such as molecular sieves for example) before returning to the reaction media. Since the adsorption agent is not directly in the reaction media, it does not affect at any time the different products of the reaction or the biocatalyst during the reaction or their recovery at the end of the reaction. Furthermore, the adsorption agent is very easily recoverable and reusable many times after just simple drying. Lowering the pressure permits to have the solvent refluxing at the optimum temperature of the biocatalyst.

This process allows the use of a vast number of solvents with a large range of boiling point, from those having elevated boiling points above 100° C. at atmospheric pressure, to those having boiling points below 100° C. if the solvent forms an azeotrope with water. The preferred process temperature is dictated by the stability of the enzyme used. For example, in the case of *Candida antarctica* type B lipase, it is around 50°–70° C. The preferred pressure is the boiling pressure of the solvent at the preferred temperature when solvents have boiling point below 100° C. at atmospheric pressure and form an azeotrope with water. In the case of solvents having boiling points above 100° C. at atmospheric pressure, the pressure is lowered enough to allow boiling of the by-product water (120–300 millibars for 50°–70° C.). This approach contributes to the novelty of the process.

Thus, the proposed process directly relates to the three problems presented above:

1: it increases the contact between the two substrates by the use of a large range of solvents,
2: it eliminates the water generated by the reaction in a continuous fashion without the loss of any solvent which in turn allows the equilibrium to be displaced towards synthesis,
3: it maintains the water activity required by the enzyme given that there is no water accumulation in the media.

According to one aspect of the invention, a process for the preparation of a sugar or sugar alcohol ester of general formula I

(I)

wherein R is an alkyl group which can be saturated or unsaturated, linear or branched and substituted or unsubstituted, n is 1 to 3 and $R^1$ is derived from a sugar or a polyol containing the moiety

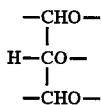

is provided, comprising reacting a sugar or a sugar polyol of formula

wherein $R^1$ and n are as defined above, with an acyl moiety of the formula

wherein R is as defined above and X is OH, OR', Cl or OOCR", in which R' and R" are an alkyl chain which can be saturated or unsaturated, linear or branched and substituted or unsubstituted, in an solvent therefor, and in the presence of an enzymatic catalyst capable of catalyzing the formation of ester bonds, and under reduced pressure sufficient to vaporize the solvent and by-product water, and continuously removing the water.

DESCRIPTION OF THE PREFERRED EMBODIMENT(S)

Figure 1:
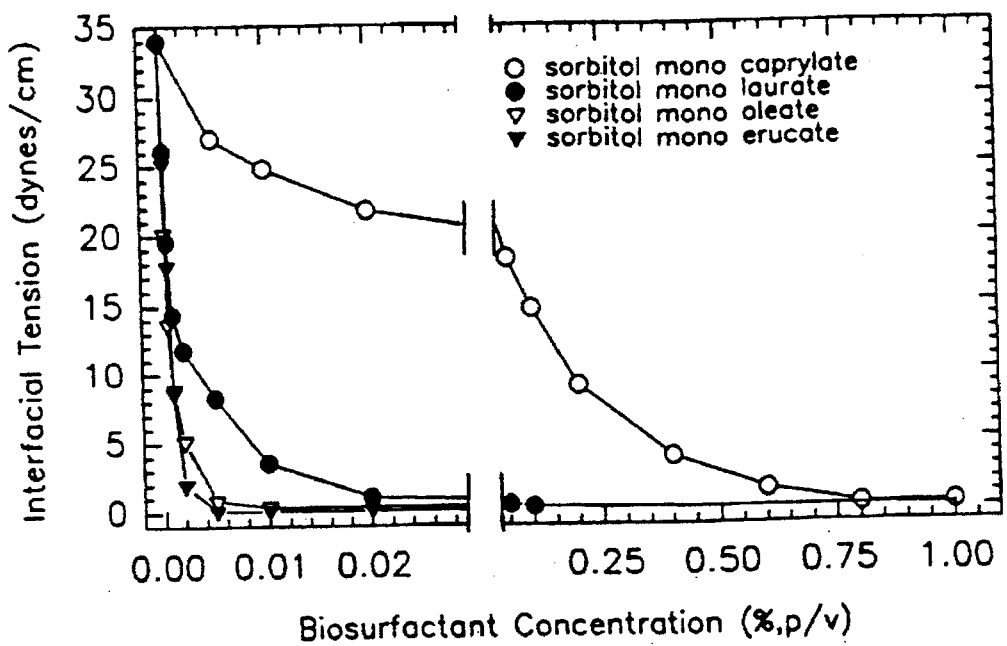
FIG. 1 is a graph which illustrates the reduction of interfacial tension between xylene and water afforded by biosurfactants prepared by a process according to the invention.

Preferably, R contains from 4 to 24 carbon atoms, and X is a good leaving group, $R^1$ can be derived from a carbohydrate (ose or oside) of general formula IIa or IIb or a polyol (especially a sugar alcohol or an oligoglycerol) of general formula III

 (IIa)

 (IIb)

 (III)

wherein $R_1$, $R_2$, $R_3$, $R_4$, and $R_5$ are the same or different, each being hydrogen, alkyl or aryl group which can contain one or more hydroxy, carboxy, carbonyl, alkoxy, amino, amido, thio, bromo, fluoro, phosphate or sulfate groups.

Specific examples of carbohydrates include fructose, where $R_1$ and $R_4$=$CH_2OH$, and $R_2$ and $R_3$=H in formula IIa, glucose, where $R_1$, $R_2$, $R_3$ and $R_4$=H, and $R_5$=$CH_2OH$ in formula IIb.

Examples of polyols can be sorbitol, where $R_1$, $R_2$, $R_3$ and $R_4$=H, and $R_5$ =H-$(CHOH)_3$ in formula III, xylitol, where $R_1$, $R_2$, $R_3$ and $R_4$=H, and $R_5$=H-$(CHOH)_2$ in formula III, glycerol, where $R_1$, $R_2$, $R_3$ $R_4$ and $R_5$=H in formula III Enzymes which may be useful as catalysts in the process of the invention are those which catalyze the formation of ester linkages. Such enzymes, from animal, vegetable, microbial or fungal origin, include esterases, lipases, proteases or any other enzyme able to catalyze esterification reactions. They may be in a soluble state, immobilized or encapsulated. They may be chemically or genetically modified in order to increase their activity in this kind of reaction.

The solvents which may be used for the process of the present invention are those which are inert towards the reaction, do not inhibit the biocatalyst and either forman azeotrope with water or have a boiling temperature above 100° C. under atmospheric pressure. Examples of such suitable solvents are the tertiary alcohols (such as methyl-2-butanol-2), the ketones (such as acetone, methyl-ethyl-ketone), the nitriles (such as acetonitrile) the alkanes (such as hexane, cyclohexane), just to mentioned a few. It will be appreciated by those skilled in the art that this list is by no means exhaustive.

The proposed process can be carried out in a conventional reactor. The reactor includes a condensor and an external water-trap, for example, of the Soxhlet type, and is connected to a vacuum pump to reduce the pressure. The different reactants are placed in solution in the reactor with the chosen solvent. After addition of the biocatalyst, the mixture is allowed to reflux by lowering the pressure and increasing temperature. The chosen pressure is such that the solvent and the water produced during the reaction pass progressively into the vapour phase. They recondense in the condenser and are led to the water-trap. The water held in the solvent is then trapped by molecular sieves located externally of the reaction media in the water-trap. Thus, the solvent which is continuously dried externally and returned to the reaction media, is anhydrous. At the end of the reaction, the biocatalyst is removed (by filtration for example), the solvent dried under reduced pressure and the desired product recovered.

The water generated by the reaction is continuously removed as it is produced without any solvent loss, which displaces the reaction equilibrium towards synthesis, and wherein the necessary activity required by the enzyme is maintained as there is no water accumulation in the media.

The present invention is further illustrated in the following examples but it should be understood that they do not in any way limit the invention.

EXAMPLE 1

Preparation Of Sorbitol Monooleate

Oleic acid (0.156 g, 0.55 mmole) and sorbitol (1.010 g, 5.55 mmole) are dissolved in methyl-2-butanol-2 (100 ml). The soxhlet extractor contains molecular sieves (3Å) and 50 ml of additional methyl-2-butanol-2. 1 g of Novozym 435 (type B lipase of *Candida antarctica* manufactured by Novo Ind.) is added and the reaction is performed under 100 mbar at 60° C. to have the solvent refluxing. The progress of the reaction and quantification of each component are monitored by HPLC using laurophenone as an internal standard. At the end of the reaction, the enzyme is removed by filtration.

Oleic acid conversion is 98.5% in 24 hours. The yield in pure sorbitol monooleate is equal to 95.6%.

EXAMPLE 2–16

In the following examples, the conditions in Example 1 have been modified to illustrate the large scale of application of the process described in this invention. The following factors have been modified:

the molar ratio of hydroxyl donor/acyl donor, the nature of the hydroxyl donor (sugar or sugar alcohol), the nature of the acyl donor (fatty acid, fatty ester), the biocatalyst, the solvent.

Conditions used and obtained results are summarized in Table I.

In Table I, the numbers used have the following meanings:

1: +50 ml of the same solvent in the Soxhlet extractor cartridge.

2: acid conversion=(#mole acid at $t_0$–#mole acid at $t_f$)/ #mole acid at $t_0$, in %.

3: yield (mole %)

4: yield in triester (mole %)

5: yield of isolated monoester formed after purification on silica column.

6: not detected under HPLC conditions used.

TABLE 1

| example | hydroxyl donor | acyl donor | molar ratio OH/COOH | biocatalyst | solvent[1] | conditions | acid[2] conversion | yield[3] in monoester (diester) |
|---|---|---|---|---|---|---|---|---|
| 1 | sorbitol 1.010 g 5.55 mmol | oleic acid 0.156 g 0.55 mmol | 10/1 | Novozym 435 1 g | 100 ml methyl-2- butanol-2 | 24 h, 60° C. 100 mbar reflux | 98.5% | 95.6% (2.8%) |
| 2 | sorbitol 1.010 g 5.55 mmol | oleic acid 0.522 g 1.85 mmol | 3/1 | Novozym 435 1 g | 100 ml methyl-2- butanol-2 | 24 h, 60° C. 100 mbar reflux | 98.8% | 91.0% (7.7%) |
| 3 | sorbitol 1.010 g 5.55 mmol | oleic acid 1.565 g 5.55 mmol | 1/1 | Novozym 435 1 g | 100 ml methyl-2- butenol-2 | 24 h, 60° C. 100 mbar reflux | 97.9% | 68.1% (29.5%) |
| 4 | sorbitol 0.337 g 1.85 mmol | oleic acid 1.565 g 5.55 mmol | 1/3 | Novozym 435 1 g | 100 ml methyl-2- butanol-2 | 24 h, 60° C. 100 mbar reflux | 67.5% | 9.6% (40.6%) |
| 5 | glucose 1.000 g 5.55 mmol | oleic acid 1.565 g 5.55 mmol | 1/1 | Novozym 435 1 g | 100 ml methyl-2- butanol-2 | 24 h, 60° C. 100 mbar reflux | 73.0% | 73.0% (0%) |
| 6 | fructose 1.000 g 5.55 mmol | oleic acid 1.565 g 5.55 mmol | 1/1 | Novozym 435 1 g | 100 ml methyl-2- butanol-2 | 24 h, 60° C. 100 mbar reflux | 92.8% | 65.1% (26.2%) |
| 7 | xylitol 0.844 g 5.55 mmol | oleic acid 1.565 g 5.55 mmol | 1/1 | Novozym 435 1 g | 100 ml methyl-2- butanol-2 | 24 h, 60° C. 100 mbar reflux | 98.0% | 65.1% (32.6%) |
| 8 | glycerol 0.511 g 5.55 mmol | oleic acid 1.565 g 5.55 mmol | 1/1 | Novozym 435 1 g | 100 ml methyl-2- butanol-2 | 24 h, 60° C. 100 mbar reflux | 99.1% | 66.6% (30.6%) (1.5%[4]) |
| 9 | sorbitol 1.010 g 5.55 mmol | caprylic acid 0.799 g 5.55 mmol | 1/1 | Novozym 435 1 g | 100 ml methyl-2- butanol-2 | 7 h, 60° C. 100 mbar reflux | — | 42%[5] |
| 10 | sorbitol 1.010 g 5.55 mmol | lauric acid 0.3705 g 1.85 mmol | 3/1 | Novozym 435 1 g | 100 ml methyl-2- butanol-2 | 24 h, 60° C. 100 mbar reflux | 98.5% | 98.5% (nd[6]) |
| 11 | sorbitol 1.010 g 5.55 mmol | erucic acid 0.626 g 1.85 mmol | 3/1 | Novozym 435 1 g | 100 ml methyl-2- butanol-2 | 24 h, 60° C. 100 mbar reflux | 99.2% | 99.2% (nd[6]) |
| 12 | fructose 1.00 g 5.55 mmol | Me-oleate 1.643 g 5.55 mmol | 1/1 | Novozym 435 1 g | 100 ml methyl-2- butanol-2 | 7 h, 60° C. 100 mbar reflux | 60.1% | 51.2% (6.2%) |

TABLE 1-continued

| example | hydroxyl donor | acyl donor | molar ratio OH/COOH | biocatalyst | solvent[1] | conditions | acid[2] conversion | yield[3] in monoester (diester) |
|---|---|---|---|---|---|---|---|---|
| 13 | sorbitol 1.010 g 5.55 mmol | Me-oleate 1.643 g 5.55 mmol | 1/1 | Novozym 435 1 g | 100 ml methyl-2-butanol-2 | 7 h, 60° C. 100 mbar reflux | 47.6% | 39.1% (4.8%) |
| 14 | sorbitol 1.010 g 5.55 mmol | oleic acid 1.565 g 5.55 mmol | 1/1 | lipase SP382 1 g | 100 ml methyl-2-butanol-2 | 24 h, 60° C. 100 mbar reflux | 94.9% | 66.0% (27.7%) |
| 15 | sorbitol 1.010 g 5.55 mmol | oleic acid 1.565 g 5.55 mmol | 1/1 | Lipozyme 1 g | 100 ml methyl-2-butanol-2 | 24 h, 60° C. 100 mbar reflux | 2.6% | 2.6% (0%) |
| 16 | glucose 1.000 g 5.55 mmol | oleic acid 1.565 g 5.55 mmol | 1/1 | Novozym 435 1 g | 100 ml acetonitrile | 24 h, 60° C. 300 mbar reflux | 26.2% | 26.2% (0%) |
| 17 | glucose 1.000 g 5.55 mmol | oleic acid 1.565 g 5.55 mmol | 1/1 | Novozym 435 1 g | 100 ml acetone | 24 h, 60° C. 550 mbar reflux | 27.2% | 27.2% (0%) |

EXAMPLE 17

Characterization of the Obtained Biosurfactants

Figure 2:
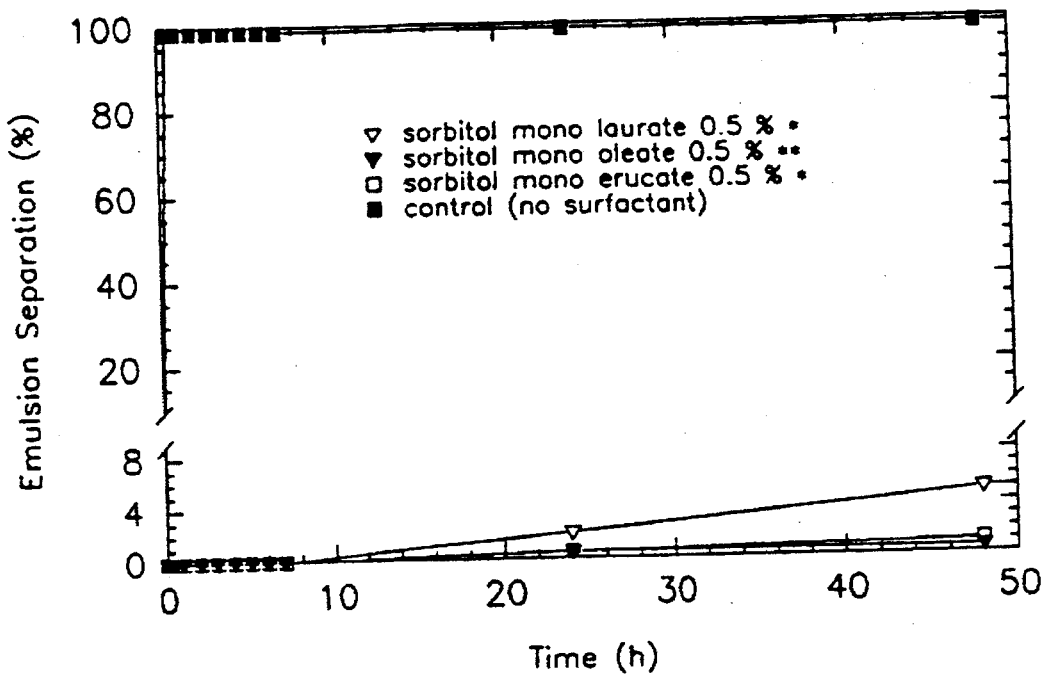
FIG. 2 is a graph illustrating the stabilization of water/xylene emulsions afforded by biosurfactants prepared by a process according to the invention.

The surfactant potential of the molecules prepared by the process described in the present invention and purified on a silica column has been evaluated by different means:

- the measurement of the surface tension between water and air (Critical micelle concentration (CMC), efficiency and effectiveness of the surfactants are presented in Table II),
- the measurement of the interfacial tension between water and xylene (results are presented on FIG. 1),
- the stabilization of water/xylene emulsions (the results of the experiments carried out at 30° C. are presented in FIG. 2). Specifically, the solution of biosurfactant in water is mixed with xylene in a Polytron (trademark) mixer for 5 min. The emulsion formed was transferred to a graduate cylinder placed at 30° C. and the separation of phases is measured as a function of time.

TABLE II

| PRODUCT | CMC | EFFICIENCY | EFFECTIVENESS |
|---|---|---|---|
| sorbitol mono-caprylate | $1.2 * 10^{-2}$M | $4.3 * 10^{-4}$M | 26.3 dynes/cm |
| sorbitol mono-laurate | $2.5 * 10^{-4}$M | $2.1 * 10^{-5}$M | 29.4 dynes/cm |
| sorbitol mono-oleate | $8.6 * 10^{-5}$M | $7.2 * 10^{-6}$M | 35.0 dynes/cm |
| sorbitol mono-erucate | $7.4 * 10^{-5}$M | $1.4 * 10^{-5}$M | 39.0 dynes/cm |
| fructose mono-oleate | $7.6 * 10^{-5}$M | $1.8 * 10^{-6}$M | 31.6 dynes/cm |
| glucose mono-oleate | $8.9 * 10^{-5}$M | $3.4 * 10^{-6}$M | 33.2 dynes/cm |
| xylitol mono-oleate | $3.5 * 10^{-5}$M | $2.1 * 10^{-6}$M | 29.7 dynes/cm |

CMC: determined from the surface tension measurements (solution of biosurfactant in water.
EFFICIENCY: taken as the concentration of surfactant needed to reduce the surface tension of water by 20 dynes/cm.
EFFECTIVENESS: minimum value to which the surfactant can lower the surface tension of water.

We claim:

1. A process for the preparation of esters of general formula I $$(R\text{—}COO\text{—})_n\text{—}R^1 \qquad (I)$$

wherein R is an alkyl group containing 4–24 carbon atoms which can be saturated or unsaturated, linear or branched and substituted or unsubstituted, n is 1 to 3 and $R^1$ is derived from a hydroxyl donor selected from a sugar and a polyol containing the moiety $$\begin{array}{c}\text{—CHO—}\\|\\ \text{H—CO—}\\|\\ \text{—CHO—}\end{array}$$

which comprises in a reactor, reacting a hydroxyl donor selected from a sugar and a polyol of formula $$R^1\text{—}(OH)_n$$

wherein $R^1$ and n are as defined above, with an acyl donor selected from a fatty acid and a fatty acid derivative of the formula $$R\text{—}CO\text{—}X$$

wherein R is as defined above and X is OH, OR', Cl or OOCR", in which R' and R" are an alkyl chain having 1–24 carbon atoms which can be saturated or unsaturated, linear or branched and substituted or unsubstituted, in a solvent therefor, wherein the solvent is inert towards the reaction and does not inhibit the catalyst, selected from the group consisting of those which have a boiling point below 100° C. and form an azeotrope with water, and those which have a boiling point above 100° C. at atmospheric pressure, and in the presence of an enzymatic catalyst capable of catalyzing the formation of ester bonds, and under reduced pressure sufficient to vaporize the solvent and by-product water, and continuously removing the water while retaining the solvent.

2. A process according to claim 1, wherein water is continuously removed by condensing the solvent/water vapour and then passing through an external water trap to extract the water before returning the solvent to the reactor.

3. A process according to claim 1, wherein the solvent is selected from the group consisting of tertiary alcohols, ketones, nitriles and alkanes.

4. A process according to claim 3, wherein the catalyst is selected from the group consisting of esterases, lipases and proteases.

5. A process according to claim 1, wherein X is a good leaving group.

6. A process according to claim 1, wherein $R^1$ contains the moiety of formula IIa

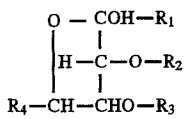

(IIa)

wherein $R_1$, $R_2$, $R_3$, $R_4$ are the same or different, each being hydrogen, lower-alkyl which can contain one or more hydroxy, carboxy, carbonyl, alkoxy, amino, amido, thio, bromo, fluoro, phosphate or sulfate groups.

7. A process according to claim 1, wherein $R^1$ contains the moiety of formula IIb

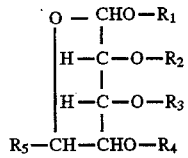

(IIb)

wherein $R_1$, $R_2$, $R_3$, $R_4$, and $R_5$ are the same or different, each being hydrogen, lower-alkyl which can contain one or more hydroxy, carboxy, carbonyl, alkoxy, amino, amido, thio, bromo, fluoro, phosphate or sulfate groups.

8. A process according to claim 1, wherein $R^1$ contains the moiety of formula III

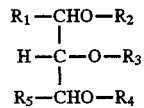

(III)

wherein $R_1$, $R_2$, $R_3$, $R_4$, and $R_5$ are the same or different, each being hydrogen, lower-alkyl which can contain one or more hydroxy, carboxy, carbonyl, alkoxy, amino, amido, thio, bromo, fluoro, phosphate or sulfate groups.

9. A process according to claim 3, wherein the catalyst is a lipase.

10. A process according to claim 9, wherein the lipase is lipase B obtained from *Candida antarctica* and the reaction temperature is 50°–70° C.

11. A process according to claim 6, wherein formula IIa, $R_1$ and $R_4$=$CH_2OH$ and $R_2$ and $R_3$=H.

12. A process according to claim 7, wherein formula IIb, $R_1$, $R_2$, $R_3$ and $R_4$=H and $R_5$=$CH_2OH$.

13. A process according to claim 8, wherein formula III, $R_1$, $R_2$, $R_3$, and $R_4$=H and $R_5$=H(CHOH)$_3$.

14. A process according to claim 8, wherein formula III, $R_1$, $R_2$, $R_3$ and $R_4$=H and $R_5$=H(CHOH)$_2$.

15. A process according to claim 8, wherein formula III, $R_1$, $R_2$, $R_3$, $R_4$, and $R_5$=H.

16. A process according to claim 1, wherein the molar ratio of hydroxyl donor: acyl donor is 1–10: 1–3.

17. A process according to claim 1, wherein the solvent is selected from the group consisting of methyl-2-butanol-2, acetonitrile and acetone.

* * * * *